(12) United States Patent
Smets et al.

(10) Patent No.: US 8,067,355 B2
(45) Date of Patent: *Nov. 29, 2011

(54) BENEFIT AGENT CONTAINING DELIVERY PARTICLES

(75) Inventors: Johan Smets, Lubbeek (BE); Peggy Dorothy Sands, Appleton, WI (US); Sandra Jacqueline Guinebretiere, Appleton, WI (US); An Pintens, Brasschaat (BE); Jiten Odhavji Dihora, Hamilton, OH (US)

(73) Assignee: Appleton Papers Inc., Appleton, WI (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/384,685

(22) Filed: Apr. 8, 2009

(65) Prior Publication Data

US 2010/0261629 A1 Oct. 14, 2010

(51) Int. Cl.
*A61K 8/11* (2006.01)
(52) U.S. Cl. ............ 512/4; 428/402.2; 428/402.21
(58) Field of Classification Search ..... 428/402–402.24; 427/213.3–213.36; 264/4–4.7; 512/1, 4
See application file for complete search history.

(56) References Cited

U.S. PATENT DOCUMENTS

| | | | |
|---|---|---|---|
| 4,002,060 A * | 1/1977 | Ogata et al. | 73/762 |
| 5,811,366 A * | 9/1998 | Chikami | 503/201 |
| 7,968,510 B2 | 6/2011 | Smets et al. | 512/4 |
| 2003/0092595 A1 | 5/2003 | Romero et al. | 510/447 |
| 2005/0026801 A1 | 2/2005 | Broeckx et al. | 510/276 |
| 2005/0112152 A1 | 5/2005 | Popplewell et al. | 424/401 |
| 2006/0248665 A1 * | 11/2006 | Pluyter et al. | 8/406 |

FOREIGN PATENT DOCUMENTS

| | | |
|---|---|---|
| EP | 1 407 753 A1 | 4/2004 |
| EP | 1 407 754 A1 | 4/2004 |
| EP | 1 533 364 A2 | 5/2005 |
| EP | 1 533 415 A1 | 5/2005 |
| EP | 1 588 760 A1 | 10/2005 |
| EP | 1 589 092 A1 | 10/2005 |
| WO | WO 02/074430 | 9/2002 |

* cited by examiner

*Primary Examiner* — James J Seidleck
*Assistant Examiner* — Saira B Haider
(74) *Attorney, Agent, or Firm* — Benjamin Mieliulis

(57) ABSTRACT

The present invention relates to benefit agent containing delivery particles, compositions comprising said particles, and processes for making and using the aforementioned particles and compositions. When employed in compositions, for example, compositions for cleaning, fabric care, or coating onto various substrates, textiles or surfaces, such particles increase the efficiency of benefit agent delivery, thereby allowing reduced amounts of benefit agents to be employed. In addition to allowing the amount of benefit agent to be reduced, such particles allow a broad range of benefit agents to be employed.

12 Claims, No Drawings

BENEFIT AGENT CONTAINING DELIVERY PARTICLES

CROSS-REFERENCES TO RELATED APPLICATIONS

This application claims priority under 35 U.S.C. §119(e) to U.S. Provisional Application Ser. No. 60/861,996 filed Nov. 30, 2006, U.S. Provisional Application Ser. No. 60/860,645 filed Nov. 22, 2006, and under 35 U.S.C. §365 as a continuation application of PCT Serial No. PCT/US07/24247 filed Nov. 20, 2007.

Appleton Papers and The Procter & Gamble Company executed a joint research agreement on or about Nov. 28, 2005 and this invention was made as a result of activities undertaken within the scope of the joint research agreement between Appleton Papers and The Procter & Gamble Company that was in effect on or before the date of the invention.

FIELD OF INVENTION

The present application relates to benefit agent containing delivery particles, compositions comprising such particles, and processes for making and using such particles and compositions.

BACKGROUND OF THE INVENTION

Benefit agents, such as perfumes, silicones, waxes, flavors, vitamins and fabric softening agents, are expensive and generally less effective when employed at high levels in personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

Accordingly, there is a need for a benefit agent containing delivery particle that provides improved benefit agent delivery efficiency.

SUMMARY OF THE INVENTION

The present invention relates to benefit agent containing delivery particles comprising a core material and a wall material that at least partially surrounds the core material. The present invention also relates to compositions comprising said particles, and processes for making and using such particles and compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the phrase "benefit agent containing delivery particle" encompasses microcapsules including perfume microcapsules.

As used herein, the terms "particle", "benefit agent containing delivery particle", "capsule" and "microcapsule" are synonymous.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicant' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefit Agent Containing Delivery Particle

Applicants discovered that the problem of achieving effective and efficient benefit agent delivery can be solved in an economical manner when a benefit agent containing delivery particle, having comprising a core material and a wall material that at least partially surrounds said core material and a certain combination of physical and chemical characteristics is employed. Such physical and chemical characteristics are defined by the Volume Weighted Fracture Strength. The delivery effectiveness and efficiency can be further tailored by selecting particles having the following Volume Weighted Fracture Strengths as listed for each application:

1.) Type 1 Benefit Agent Containing Delivery Particles (Type 1 Particles). Such particles may be employed when a benefit, for example, odor is desired in/from a wash solution. Such particles may have a Volume Weighted Fracture Strength less than about 0.8 MPa, from about 0.8 MPa to about 0.1 MPa, or even from about 0.75 MPa to about 0.25 MPa.

2.) Type 2 Benefit Agent Containing Delivery Particles (Type 2 Particles). Such particles may be employed when a benefit, for example, odor is desired from a wet situs. Such particles may have a Volume Weighted Fracture Strength from about 0.5 MPa to about 2 MPa, from about 0.8 MPa to about 1.8 MPa, or even from about 1 MPa to about 1.7 MPa.

3.) Type 3 Benefit Agent Containing Delivery Particles (Type 3 Particles). Such particles may be employed when a benefit, for example, odor is desired from a dry situs dried after being contacted with such particles. Such particles may have a Volume Weighted Fracture Strength from about 1.5 MPa or even 2 MPa to about 5 MPa, from about 1.5 MPa or even 2 MPa to about 4 MPa, or from about 1.5 MPa or even 2 MPa to about 3 MPa.

4.) Type 4 Benefit Agent Containing Delivery Particles (Type 4 Particles). Such particles may be employed when a benefit, for example, odor is desired from a situs during wear/use after such situs is contacted with such particles. Such particle may have a Volume Weighted Fracture Strength from about 5 MPa to about 16 MPa, from about 5 MPa to about 9 MPa, or even from about 6 MPa to about 8 MPa.

In short, the level of benefit at any one point may be tailored by selecting the desired amount type of each class of benefit agent containing delivery particle.

In one aspect, Applicants disclose a particle composition wherein the total volume weight of the particles is 100% and the volume weight of each type of particle may be as follows:

Type 1 Particles. From about 0% to about 100%, from about 5% to about 50%, or even from about 5% to about 25%;

Type 2 Particles: From about 0% to about 100%, from about 5% to about 50%, or even from about 5% to about 25%;

Type 3 Particles: From about 0% to 100%, from about 5% to about 90%, or even from about 5% to about 25%; and Type 4 Particles: From about 0% to about 100%, from about 5% to about 50%, or even from about 5% to about 25%.

With the proviso that the sum of the percentage of the Type 1, 2, 3 and 4 Benefit Agent Containing Delivery Particles is always 100%—such sum cannot exceed or be less than 100%.

In one aspect, a consumer product comprising from about 0.001% to about 25%, from about 0.001% to about 10%, or from about 0.01% to about 3%, based on total consumer product mass weight, of the aforementioned particle composition is disclosed.

In one aspect, a cleaning composition comprising from about 0.005% to about 10%, from about 0.01% to about 3%, or from about 0.1% to about 1% based on total cleaning composition mass weight of the aforementioned particle composition is disclosed.

In one aspect, a fabric care composition comprising from about 0.005% to about 10%, from about 0.01% to about 3%, or from about 0.1% to about 1% based on total fabric care mass weight of the aforementioned particle composition is disclosed.

In one aspect, when the aforementioned particle composition is employed in a consumer product, for example a liquid consumer product, the particle composition may have a deposition of at least 10%, 20%, 30%, 40%, 50%, 60%, 70%, 80%, 90%, or even 100%.

In one aspect, when the aforementioned particle composition is employed in a consumer product, for example a liquid consumer product, the particle composition may have less than 50%, 40%, 30%, 20%, 10% or even 0% leakage of the encapsulated benefit agent from the microcapsules of said particle composition into said consumer product.

Useful wall materials include materials selected from the group consisting of polyethylenes, polyamides, polystyrenes, polyisoprenes, polycarbonates, polyesters, polyacrylates, polyureas, polyurethanes, polyolefins, polysaccharides, epoxy resins, vinyl polymers, and mixtures thereof. In one aspect, useful wall materials include materials that are sufficiently impervious to the core material and the materials in the environment in which the benefit agent containing delivery particle will be employed, to permit the delivery benefit to be obtained. Suitable impervious wall materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In one aspect, the wall material comprises melamine cross-linked with formaldehyde.

Useful core materials include perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof. In one aspect, said perfume raw material is selected from the group consisting of alcohols, ketones, aldehydes, esters, ethers, nitrites alkenes. In one aspect the core material comprises a perfume. In one aspect, said perfume comprises perfume raw materials selected from the group consisting of alcohols, ketones, aldehydes, esters, ethers, nitrites alkenes and mixtures thereof. In one aspect, said perfume may comprise a perfume raw material selected from the group consisting of perfume raw materials having a boiling point (B.P.) lower than about 250° C. and a ClogP lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials, perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. In one aspect, said perfume comprises a perfume raw material having B.P. of lower than about 250° C. In one aspect, said perfume comprises a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

In one aspect, said perfume comprises a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

In one aspect, said benefit agent delivery particles' core material comprises:
  a.) a perfume composition having a Clog P of less than 4.5;
  b.) a perfume composition comprising, based on total perfume composition weight, 60% perfume materials having a Clog P of less than 4.0;
  c.) a perfume composition comprising, based on total perfume composition weight, 35% perfume materials having a Clog P of less than 3.5;
  d.) a perfume composition comprising, based on total perfume composition weight, 40% perfume materials having a Clog P of less than 4.0 and at least 1% perfume materials having a Clog P of less than 2.0;
  e.) a perfume composition comprising, based on total perfume composition weight, 40% perfume materials having a Clog P of less than 4.0 and at least 15% perfume materials having a Clog P of less than 3.0;
  f.) a perfume composition comprising, based on total perfume composition weight, at least 1% butanoate esters and at least 1% of pentanoate esters;
  g.) a perfume composition comprising, based on total perfume composition weight, at least 2% of an ester comprising an allyl moiety and at least 10% of another perfume comprising an ester moiety;
  h.) a perfume composition comprising, based on total perfume composition weight, at least 1% of an aldehyde comprising an alkyl chain moiety;
  i.) a perfume composition comprising, based on total perfume composition weight, at least 2% of a butanoate ester;
  j.) a perfume composition comprising, based on total perfume composition weight, at least 1% of a pentanoate ester;
  k.) a perfume composition comprising, based on total perfume composition weight, at least 3% of an ester comprising an allyl moiety and 1% of an aldehyde comprising an alkyl chain moiety;
  l.) a perfume composition comprising, based on total perfume composition weight, at least 25% of a perfume comprising an ester moiety and 1% of an aldehyde comprising an alkyl chain moiety;
  m.) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
  n.) a perfume composition comprising, based on total perfume composition weight, at least 0.1% of tridec-2-enonitrile, and mandaril, and mixtures thereof;
  o.) a perfume composition comprising, based on total perfume composition weight, at least 2% of a material selected from 3,7-dimethyl-6-octene nitrile, 2-cyclohexylidene-2-phenylacetonitrile and mixtures thereof;
  p.) a perfume composition comprising, based on total perfume composition weight, at least 80% of one or more perfumes comprising a moiety selected from the group consisting of esters, aldehydes, ionones, nitrites, ketones and combinations thereof;
  q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-metnh-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bicyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate; 4-undecanone; 5-heptyldihydro-2(3h)-furanone; 1,6-nonadien-3-ol,3,7dimethyl-; 3,7-dimethylocta-1,6-dien-3-o; 3-cyclohexene-1-carboxaldehyde,dimethyl-;3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2- methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bicyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate, 4-undecanolide; 5-heptyldihydro-2(3h)-furanone; 5-hydroxydodecanoic acid; decalactones; undecalactones, 1,6-nonadien-3-ol, 3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro [4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;

s.) a perfume composition comprising, based on total perfume composition weight, a t least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

t.) a perfume composition comprising, based on total perfume composition weight, less than 10% perfumes having a Clog P greater than 5.0;

u.) a perfume composition comprising geranyl palmitate; or v.) a perfume composition comprising a first and an optional second material, said first material having:

(i) a Clog P of at least 2;
(ii) a boiling point of less than about 280 ° C.; and
second optional second material, when present, having
(i) a Clog P of less than 2.5; and
(ii) a ODT of less than about 100 ppb.

The perfume raw materials and accords may be obtained from one or more of the following companies Firmenich (Geneva, Switzerland), Givaudan (Argenteuil, France), IFF (Hazlet, N.J.), Quest (Mount Olive, N.J.), Bedoukian (Danbury, Conn.), Sigma Aldrich (St. Louis, Mo.), Millennium Specialty Chemicals (Olympia Fields, Ill.), Polarone International (Jersey City, N.J.), Fragrance Resources (Keyport, N.J.), and Aroma & Flavor Specialties (Danbury, Conn).

Process of Making Benefit Agent Containing Delivery Particles

The particle disclosed in the present application may be made via the teachings of U.S. Pat. No. 6,592,990 B2 and/or U.S. Pat. No. 6,544,926 B1 and the examples disclosed herein.

Anionic emulsifiers are typically used during the particle making process to emulsify the benefit agent prior to microcapsule formation. While not being bound by theory, it is believed that the anionic materials adversely interact with the cationic surfactant actives that are often found in compositions such as fabric care compositions—this may yield an aesthetically unpleasing aggregation of particles that are employed in said composition. In addition to the unacceptable aesthetics, such aggregates may result in rapid phase separation of the particles from the bulk phase. Applicants discovered that such aggregates can be prevented by the addition of certain aggregate inhibiting materials including materials selected from the group consisting of salts, polymers and mixtures thereof. Useful aggregate inhibiting materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium calcium acetate, calcium bromide; trivalent salts, such as aluminum salts, for example, aluminum sulfate, aluminum phosphate, aluminum chloride n-hydrate and polymers that have the ability to suspend anionic particles such as soil suspension polymers, for example, (polyethylene imines, alkoxylated polyethylene imines, polyquaternium-6 and polyquaternium-7.

In one aspect of the invention, benefit agent containing delivery particles are manufactured and are subsequently coated with a material to reduce the rate of leakage of the benefit agent from the particles when the particles are subjected to a bulk environment containing, for example, surfactants, polymers, and solvents. Non-limiting examples of coating materials that can serve as barrier materials include materials selected from the group consisting of polyvinyl pyrrolidone homopolymer, and its various copolymers with styrene, vinyl acetate, imidazole, primary and secondary amine containing monomers, methyl acrylate, polyvinyl acetal, maleic anhydride; polyvinyl alcohol homopolymer, and its various copolymers with vinyl acetate, 2-acrylamide-2-methylpropane sulfonate, primary and secondary amine containing monomers, imidazoles, methyl acrylate; polyacrylamides; polyacrylic acids; microcrystalline waxes; paraffin waxes; modified polysaccharides such as waxy maize or dent corn starch, octenyl succinated starches, derivatized starches such as hydroxyethylated or hydroxypropylated starches, carrageenan, guar gum, pectin, xanthan gum; modified celluloses such as hydrolyzed cellulose acetate, hydroxy propyl cellulose, methyl cellulose, and the like; modified proteins such as gelatin; hydrogenated and non-hydrogenated polyalkenes; fatty acids; hardened shells such as urea crosslinked with formaldehyde, gelatin-polyphosphate, melamine-formaldehyde, polyvinyl alcohol cross-linked with sodium tetraborate or gluteraldehyde; latexes of styrene-butadiene, ethyl cellulose, inorganic materials such as clays including magnesium silicates, aluminosilicates; sodium silicates, and the like; and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A. In one aspect wherein the particle is employed in a fabric conditioning composition, the coating material comprises sodium silicate. While not being bound by theory, it is believed that sodium silicate's solubility at high pH, but poor solubility at low pH makes it an ideal material for use on particles that may be used in compositions that are formulated at pH below 7 but used in an environment wherein the pH is greater or equal to 7. The benefit agent containing delivery particles made be made by following the procedure described in U.S. Pat. No. 6,592,990. However, the coating aspect of the present invention is not limited to the benefit agent containing delivery particles of the present invention as any benefit agent containing delivery particle may benefit from the coatings and coating processes disclosed herein.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderbom, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA).

Formaldehyde Scavenging

In one aspect, benefit agent containing delivery particles may be combined with a formaldehyde scavenger. In one aspect, such benefit agent containing delivery particles may comprise the benefit agent containing delivery particles of the present invention. Suitable formaldehyde scavengers include materials selected from the group consisting of sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa. U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

In another aspect, such formaldehyde scavengers may be combined with a slurry containing said benefit agent containing delivery particle, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation, In one aspect, one or more of the aforementioned formaldehyde scavengers may be combined with a liquid fabric enhancing product containing a benefit agent containing delivery particle at a level, based on total liquid fabric enhancing product weight, of from 0.005% to about 0.8%, alternatively from about 0.03% to about 0.4%, alternatively from about 0.06% to about 0.25% of the product formulation In one aspect, such formaldehyde scavengers may be combined with a liquid laundry detergent product containing a benefit agent containing delivery particle, said scavengers being selected from the group consisting of sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In one aspect, such formaldehyde scavengers may be combined with a hair conditioning product containing a benefit agent containing delivery particle, at a level, based on total hair conditioning product weight, of from about 0.003 wt. % to about 0.30 wt. %, from about 0.03 wt. % to about 0.20 wt. % or even from about 0.06 wt. % to about 0.14 wt. %., said selection of scavengers being identical to the list of scavengers in the previous paragraph relating to a liquid laundry detergent product.

Compositions Comprising Benefit Agent Containing Delivery Particles

Applicants' compositions comprise an embodiment of the particle disclosed in the present application. In one aspect, said composition is a consumer product. While the precise level of particle that is employed depends on the type and end use of the composition, a composition may comprise from about 0.01 to about 10, from about 0.1 to about 10, or even from about 0.2 to about 5 weight % of said particle based on total composition weight. In one aspect, a cleaning composition may comprise, from about 0.1 to about 1 weight % of such particle based on total cleaning composition weight of such particle. In one aspect, a fabric treatment composition may comprise, based on total fabric treatment composition weight, form about 0.01 to about 10% of such particle.

Aspects of the invention include the use of the particles of the present invention in laundry detergent compositions (e.g., TIDE™), hard surface cleaners (e.g., MR CLEAN™), automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Fabric treatment compositions disclosed herein typically comprise a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' delivery particles and FSAs. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Processes of Making and Using Compositions

The compositions of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303 all of which are incorporated herein by reference.

Method of Use

Compositions containing the benefit agent delivery particle disclosed herein can be used to clean or treat a situs inter alia a surface or fabric. Typically at least a portion of the situs is contacted with an embodiment of Applicants' composition, in neat form or diluted in a liquor or dispersed in a binder material, for example, a wash liquor, or a dispersed particle composition and binder. The situs may be optionally washed and/or rinsed before and/or after contact. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90 ° C. and, when the situs comprises a fabric, the water to fabric ratio is typically from about 1:1 to about 30:1.

When the particle composition comprises particles dispersed in binder, the dispersed particle composition and binder can be dried or cured on the situs. A releasing force such as pressure, friction, heat, actinic radiation, laser light, electromagnetic radiation, chemical degradation, or ultrasonics can be used to release the core contents from the particles.

Some applications employ parts per million of particles to binder where trace amounts of core are sufficient for the application. In other applications such compositions are employed at concentration of from 0.001% by weight of the composition to 90% by weight capsules in a slurry of capsules and binder. Binder can be used at a ratio of particles to binder at from 3:1 to about 0.0001 to 1 by weight depending on the intended application. When the situs comprises a polymeric substrate the capsules are used at a ratio of from 1.5:1 and preferably a range from 0.001:1 to 1.2:1. With a heavier paper surface, the particles and binder can be applied at a coat rate of from 2.5 to 12 grams per square meter, preferably 3 to 9 gsm. with the particles being at from 0.001 to 75% of the coating by weight.

Test Methods

It is understood that the test methods that are disclosed in the Test Methods Section of the present application should be used to determine the respective values of the parameters of Applicants' invention as such invention is described and claimed herein.

(1) Fracture Strength
   a.) Place 1 gram of particles in 1 liter of distilled deionized (DI) water.
   b.) Permit the particles to remain in the DI water for 10 minutes and then recover the particles by filtration.
   c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture strength by dividing the average rupture force (in Newtons) by the average cross-sectional area of the spherical particle ($\pi r^2$, where r is the radius of the particle before compression), said average cross-sectional area being determined as follows:
  (i) Place 1 gram of particles in 1 liter of distilled deionized (DI) water.
  (ii) Permit the particles to remain in the DI water for 10 minutes and then recover the particles by filtration.
  (iii) Determine the particle size distribution of the particle sample by measuring the particle size of 50 individual particles using the experimental apparatus and method of Zhang, Z.; Sun, G; "Mechanical Properties of Melamine-Formaldehyde microcapsules," J. Microencapsulation, vol 18, no. 5, pages 593-602, 2001.
  (iv) Average the 50 independent particle diameter measurements to obtain an average particle diameter.
d) For a capsule slurry the sample is divided into three particle size fractions covering the particle size distribution. Per particle size fraction about 30 fracture strengths are determined.

(2) ClogP

The "calculated logp" (ClogP) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via a AccuSizer 780/AD supplied by Particle Sizing Systems of Santa Barbara Calif., U.S.A.

Procedure:
1) put the sensor in a cold state by flushing water through the sensor
2) confirm background counts are less than 100 (if got more than 100, continue the flush)
3) prepare particle standard: pipette approx. 1 ml of shaken particles into blender filled with approx. 2 cups of DI water. Blend it. Pipette approx. 1 ml of diluted blended particles into 50 ml DI water.
4) measure particle standard: pipette approx. 1 ml of double diluted standard into Accusizer bulb. Press the start measurement-Autodilution button. Confirm particles counts are more than 9200 by looking in the status bar. If counts are less than 9200, press stop and inject more sample.
5) immediately after measurement, inject one full pipette of soap (5% Micro 90) into bulb and press the Start Automatic Flush Cycles button.

(5) Volume Weighted Fracture Strength (VWFS)

VWFS=(fracture strength$_1$×volume fraction$_1$)+(fracture strength$_2$×volume fraction$_2$)+(fracture strength$_3$×volume fraction$_3$)

Fracture strength$_1$=average fracture strength measured from a pool of 10 microcapsules (with similar particle size)

Volume fraction$_1$=volume fraction determined via Accusizer of particle distribution corresponding to fracture strength$_1$ The spread around the fracture strength to determine the volume fraction is determined as follows:

For particle batches with a mean particle sizes of about 15 um a spread of about 10 um is used, for particle batches with a mean particle sizes of about 30 um and above, a spread of about 10 to 15 um is used

EXAMPLES

| Particle batch | Mean Particle Size | Fracture Strength Determination at 3 particle sizes | Volume Fractions | Volume Fracture Strength |
|---|---|---|---|---|
| Melamine based polyurea | 31 micron | 21 micron: 1.8 MPa<br>31 micron: 1.6 MPa<br>41 micron: 1.2 MPa | 1 to 25 micron 30%<br>25 to 36 micron 40%<br>36 to 50 micron 30% | 1.5 MPa |

(6) Benefit Agent Leakage Test
  a.) Obtain 2, one gram samples of benefit agent particle composition.
  b.) Add 1 gram (Sample 1) of particle composition to 99 grams of product matrix that the particle will be employed in and with the second sample immediately proceed to Step d below.
  c.) Age the particle containing product matrix (Sample 1) of a.) above for 2 weeks at 35° C. in a sealed, glass jar.
  d.) Recover the particle composition's particles from the product matrix of c.) (Sample 1 in product matrix) and from particle composition (Sample 2) above by filtration.
  e.) Treat each particle sample from d.) above with a solvent that will extract all the benefit agent from each samples' particles.
  f.) Inject the benefit agent containing solvent from each sample from e.) above into a Gas Chromatograph and integrate the peak areas to determine the total quantity of benefit agent extracted from each sample.
  g.) The benefit agent leakage is defined as:
    Value from f.) above for Sample 2—Value from f.) above for Sample 1.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

80 wt % Core/20 wt % Wall Urea Based Polyurea Capsule 2 grams of Urea (Sigma Aldrich of Milwaukee, Wis.) is dissolved in 20 g deionized water. 1 gram of resorcinol (Sigma Aldrich of Milwaukee, Wis.) is added to the homogeneous urea solution. 20 g of 37 wt % formaldehyde solution (Sigma Aldrich of Milwaukee, Wis.) is added to the solution, and the pH of the slurry is adjusted to 8.0 using 1M sodium hydroxide solution (Sigma Aldrich of Milwaukee, Wis.). The reactants are allowed to sit at 35° C. for 2 hours. In a separate beaker, 80 grams of fragrance oil is added slowly to the urea-formaldehyde solution. The mixture is agitated using a Janke & Kunkel Laboretechnik mixer using a pitched, 3-blade agitator to achieve a 31 micron mean oil droplet size distribution. The pH of the slurry is adjusted to 3.0 using 1M Hydrochloric Acid to initiate the condensation reaction. The solution is heated to 65° C. and allowed to react in a constant temperature water bath, while slowly agitating the contents of the mixture. The contents are allowed to react for 4 hours at 65° C.

The Volume Average Fracture Strength Fracture is determined to be 1.5 MPa.

Example 2

85% Core/15 wt % Wall Melamine based Polyurea capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid.

178 grams of the capsule core material which comprise a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 16 micron. The temperature of the mixture is gradually raised to 65 degrees Centigrade, and is maintained at this temperature overnight with continuous stirring to initiate and complete encapsulation.

To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

The Volume Average Fracture Strength Fracture is determined to be 3.3 MPa.

Example 3

90% Core/10 wt % Wall Melamine based Polyurea Capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid.

280 grams of the capsule core material which comprise a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 18 micron. The temperature of the mixture is gradually raised to 65 degrees Centigrade, and is maintained at this temperature overnight with continuous stirring to initiate and complete encapsulation.

To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

The Volume Average Fracture Strength Fracture is determined to be 0.5 MPa.

Example 4

80% Core/20 wt % Wall Melamine Based Polyurea capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid.

125 grams of the capsule core material which comprises a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 15 micron. The temperature of the mixture is gradually raised to 65 degrees Centigrade, and is maintained at this temperature overnight with continuous stirring to initiate and complete encapsulation.

To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

The Volume Average Fracture Strength Fracture is determined to be 9.5 MPa.

Example 5

85% Core/15 wt % Wall Melamine Based Polyurea Capsule

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid.

178 grams of the capsule core material which comprise a fragrance oil is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, Cytec). This mixture is added to the above described fragrance oil-in-water emulsion with stirring at a temperature of 45 degrees Centigrade. High speed blending is used to achieve a volume-mean particle size of 15 microns. The temperature of the mixture is gradually raised to 65 degrees Centigrade, and is maintained at this temperature overnight with continuous stirring to initiate and complete encapsulation.

To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

The Volume Average Fracture Strength Fracture is determined to be 15.1 MPa.

Example 6

80 wt % Core/20 wt % Wall Melamine Formaldehyde Capsule 18 grams of a blend of 50% butyl acrylate-acrylic acid copolymer emulsifier (Colloid C351, 25% solids, pka 4.5-4.7, Kemira) and 50% polyacrylic acid (35% solids, pKa 1.5-2.5, Aldrich) is dissolved and mixed in 200 grams deionized water. The pH of the solution is adjusted to pH of 3.5 with sodium hydroxide solution. 6.5 grams of partially methylated methylol melamine resin (Cymel 385, 80% solids Cytec) is added to the emulsifier solution. 200 grams of perfume oil is added to the previous mixture under mechanical agitation and the temperature is raised to 60° C. After mixing at higher speed until a stable emulsion is obtained, the second solution and 3.5 grams of sodium sulfate salt are poured into the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.6, 30 grams of partially methylated methylol melamine resin (Cymel 385, 80% Cytec). This mixture is heated to 75° C. and maintained 6 hours with continuous stirring to complete the encapsulation process. 23 grams of acetoacetamide (Sigma-Aldrich, Saint Louis, Mo., U.S.A.) is added to the suspension.

Example 7

80 wt % Core/20 wt % Wall Melamine Formaldehyde Capsule 20 grams of butyl acrylate-acrylic acid copolymer emulsifier (Colloid C351, 25% solids, pKa 4.5-4.7, Kemira) is dissolved and mixed in 200 grams deionized water. The pH of the solution is adjusted to pH of 5.5 with sodium hydroxide solution. 6 grams of partially methylated methylol melamine resin (Cymel 385, 80% solids, Cytec) is added to the emulsifier solution. 200 grams of perfume oil is added to the previous mixture under mechanical agitation and the temperature is raised to 55° C. After mixing at higher speed until a stable emulsion is obtained, the second solution and 9 grams of sodium sulfate salt is added to the emulsion. This second solution contains 8 grams of polyacrylic acid (35% solids, pka 1.5-2.5, Aldrich), 120 grams of distilled water, sodium hydroxide solution to adjust pH to 4.4, 35 grams of partially methylated methylol melamine resin (Cymel 385, 80% solids, Cytec). This mixture is heated to 80° C. and maintained 4 hours with continuous stirring to complete the encapsulation process. 23 grams of acetoacetamide (Sigma-Aldrich, Saint Louis, Mo., U.S.A.) is added to the suspension.

Example 8

Non-limiting examples of product formulations containing microcapsules summarized in the following table.

| (% wt) | EXAMPLES | | | | | | | | | |
|---|---|---|---|---|---|---|---|---|---|---|
| | XI | XII | XIII | XIV | XV | XVI | XVII | XVIII | XIX | XX |
| FSA[a] | 14 | 16.47 | 14 | 12 | 12 | 16.47 | — | — | 5 | 5 |
| FSA[b] | | | | | — | | 3.00 | — | — | — |
| FSA[c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch[d] | 1.25 | 1.47 | 2.00 | 1.25 | — | 2.30 | 0.5 | 0.70 | 0.71 | 0.42 |
| Microcapsule (% active)* | 0.6 | 0.75 | 0.6 | 0.75 | 0.37 | 0.60 | 0.37 | 0.6 | 0.37 | 0.37 |
| Formaldehyde Scavenger[e] | 0.40 | 0.13 | 0.065 | 0.25 | 0.03 | 0.030 | 0.030 | 0.065 | 0.03 | 0.03 |
| Phase Stabilizing Polymer[f] | 0.21 | 0.25 | 0.21 | 0.21 | 0.14 | — | — | 0.14 | — | — |
| Suds Suppressor[g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant[l] | 0.01 | 0.01 | 0.01 | 0.01 | 0.01 | 0.01 | 0.01 | 0.01 | 0.01 | 0.01 |

-continued

| (% wt) | XI | XII | XIII | XIV | XV | XVI | XVII | XVIII | XIX | XX |
|---|---|---|---|---|---|---|---|---|---|---|
| | | | | EXAMPLES | | | | | | |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a]N,N-di(tallowoyloxyethyl)-N,N-dimethylammonium chloride.
[b]Methyl bis(tallow amidoethyl)2-hydroxyethyl ammonium methyl sulfate.
[c]Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d]Cationic high amylose maize starch available from National Starch under the trade name CATO ®.
[e]The formaldehyde scavenger is acetoacetamide available from Aldrich.
[f]Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g]SE39 from Wacker
[h]Diethylenetriaminepentaacetic acid.
[i]KATHON ® CG available from Rohm and Haas Co. "PPM" is "parts per million."
[j]Gluteraldehyde
[k]Silicone antifoam agent available from Dow Corning Corp. under the trade name DC2310.
[l]Hydrophobically-modified ethoxylated urethane available from Rohm and Haas under the tradename Aculan 44.
*Suitable combinations of the microcapsules provided in Examples 1 through 7.

Example 9

Microcapsules in Dry Laundry Formulations

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |

-continued

| Component | % w/w granular laundry detergent composition | | | | | | |
|---|---|---|---|---|---|---|---|
| | A | B | C | D | E | F | G |
| Perfume microcapsules* | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*Microcapsule added as 35% active slurry. Core/wall ratio can range from 80/20 up to 90/10 and average particle diameter can range from 5 μm to 50 μm Example 10

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules* | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

*Perfume Microcapsules in accordance with the teaching of the present specification.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A particle composition comprising one or more particles comprising a core material and a wall, material that at least partially surrounds said core material, said particles being selected from the group consisting of Type 1 particles, Type 2 particles, Type 3 particles, Type 4 particles and mixtures thereof;
 wherein the Type 1 particles have a Volume Weighted Fracture Strength of less than 0.8 MPa;
 wherein the Type 2 particles have a Volume Weighted Fracture Strength of from 0.5 MPa to about 2 MPa;
 wherein the Type 3 particles have a Volume Weighted Fracture Strength of from about 1.5 MPa to about 5 MPa;
 wherein the Type 4 particles have a Volume Weighted Fracture Strength of from about 5 MPa to about 16 MPa,
 wherein the volume weight of each type of particle in said particle composition is a follows:
  Type 1 Particles: from about 5% to about 50%;
  Type 2 Particles: from about 5% to about 50%;
  Type 3 Particles: from about 5% to about 90%; and
  Type 4 Particles: from about 5% to about 50%.

2. The composition of claim 1, wherein said particles' core material comprises a material selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, glycerin, and natural actives, antibacterial actives, antiperspirant actives, cationic polymers, dyes and mixtures thereof.

3. The composition of claim 1 wherein said particles' wall material comprises a material selected from the group consisting of polyamine, polyurea, polyurethane polysaccharides and modified polysaccharides, gel forming proteins, modified celluloses, carboxylic acid containing acrylic polymers, gelatin, gum arabic, urea crosslinked with formaldehyde, urea crosslinked with gluteraldehyde, melamine crosslinked with formaldehyde, chitin and chitosan and modified chitin and modified chitosan, sodium alginate, latexes, silicon dioxide, sodium silicates and mixtures thereof.

4. The composition of claim 1 wherein said particle comprises at least 1 weight % of a benefit agent.

5. The composition of claim 1 wherein said particles' core material comprises, based on total core material weight, at least about 20 wt % benefit agent.

6. The composition of claim 5 said benefit agent comprises a perfume composition, said particles comprising, based on total particle weight, from about 20 weight % to about 95 weight % of said perfume composition.

7. The composition of claim 6, wherein said perfume composition comprises a Quadrant III perfume raw material.

8. The composition of claim 1 wherein said particles' comprise a core material comprising:
 a.) a perfume composition having a Clog P of less than 4.5;
 b.) a perfume composition comprising, based on total perfume composition weight, 60% perfume materials having a Clog P of less than 4.0;
 c.) a perfume composition comprising, based on total perfume composition weight, 35% perfume materials having a Clog P of less than 3.5;
 d.) a perfume composition comprising, based on total perfume composition weight, 40% perfume materials having a Clog P of less than 4.0 and at least 1% perfume materials having a Clog P of less than 2.0;
 e.) a perfume composition comprising, based on total perfume composition weight, 40% perfume materials having a Clog P of less than 4.0 and at least 15% perfume materials having a Clog P of less than 3.0;
 f.) a perfume composition comprising, based on total perfume composition weight, at least 1% butanoate esters and at least 1% of pentanoate esters;
 g.) a perfume composition comprising, based on total perfume composition weight, at least 2% of an ester comprising an allyl moiety and at least 10% of another perfume comprising an ester moiety;
 h.) a perfume composition comprising, based on total perfume composition weight, at least 1% of an aldehyde comprising an alkyl chain moiety;
 i.) a perfume composition comprising, based on total perfume composition weight, at least 2% of a butanoate ester;
 j.) a perfume composition comprising, based on total perfume composition weight, at least 1% of a pentanoate ester;
 k.) a perfume composition comprising, based on total perfume composition weight, at least 3% of an ester comprising an allyl moiety and 1% of an aldehyde comprising an alkyl chain moiety;
 l.) a perfume composition comprising, based on total perfume composition weight, at least 25% of a perfume comprising an ester moiety and 1% of an aldehyde comprising an alkyl chain moiety;
 m.) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one, 3-methyl-4-(2,6,6-trimethyl-1-cyclohexen-2-yl)- and mixtures thereof;
 n.) a perfume composition comprising, based on total perfume composition weight, at least 0.1% of tridec-2-enonitrile, and mandaril, and mixtures thereof;
 o.) a perfume composition comprising, based on total perfume composition weight, at least 2% of a material selected from 3,7-dimethyl-6-octene nitrile, 2-cyclohexylidene-2-phenylacetonitrile and mixtures thereof;
 p.) a perfume composition comprising, based on total perfume composition weight, at least 80% of one or more perfumes comprising a moiety selected from the group consisting of esters, aldehydes, ionones, nitriles, ketones and combinations thereof;
 q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-metnh-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid, 3-(1-methylethyl)-ethyl ester; bycyclo [2.2.1]heptan-2-ol, 1,7,7-trimethyl-, acetate; 1,5-dimethyl-1-ethenylhex-4-eny-lacetate; hexyl 2-methyl propanoate; ethyl-2-methylbutanoate; 4-undecanone; 5-heptyldihydro-2(3h)-furanone; 1,6-nonadien-3-ol, 3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl, 1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2- s.) propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate, 4-undecanolide; 5-heptyldihydro-2(3h)-furanone; 5-hydroxydodecanoic acid; decalactones; undecalactones, 1,6-nonadien-3-ol,3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, t.) cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;

u.) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

v.) a perfume composition comprising, based on total perfume composition weight, less than 10% perfumes having a Clog P greater than 5.0;

w.) a perfume composition comprising geranyl palmitate; or x.) a perfume composition comprising a first and an optional second material, said first material having:
(i) a Clog P of at least 2;
(ii) a boiling point of less than about 280° C.; and
second optional second material, when present, having
(i) a Clog P of less than 2.5; and
(ii) a ODT of less than about 100 ppb.

9. A method of applying a particle composition to a situs, said method comprising
a.) optionally washing and/or rinsing said situs;
b.) optionally dispersing the particle composition in a binder material;
c.) contacting said situs with a composition according to claim 1;
d.) drying or curing the dispersed particle composition and binder;
e.) applying a releasing force to the particle composition to release the particles' core material; and
f.) optionally washing and/or rinsing said situs.

10. A situs treated with a composition according to claim 1.

11. A composition according to claim 1 said composition comprising a formaldehyde scavenger.

12. The method according to claim 9 wherein the releasing force is selected from pressure, friction, heat, actinic radiation; laser light, electromagnetic radiation, chemical degradation or ultrasonic.

* * * * *